(12) United States Patent
Man et al.

(10) Patent No.: US 9,885,718 B2
(45) Date of Patent: Feb. 6, 2018

(54) SPECIFIC BIOMARKER SET FOR NON-INVASIVE DIAGNOSIS OF LIVER CANCER

(71) Applicant: Dragon Victory Development Ltd., Hong Kong (HK)

(72) Inventors: Cornelia Wing Yin Man, Hong Kong (HK); Norman Fung Man Wai, Vancouver (CA); Bing Lou Wong, Irvine, CA (US); Benjamin Chi Yin Wai, Burnaby (CA)

(73) Assignee: Dragon Victory Development Ltd., Hong Kong (HK)

( * ) Notice: Subject to any disclaimer, the term of this patent is extended or adjusted under 35 U.S.C. 154(b) by 67 days.

(21) Appl. No.: 14/321,870

(22) Filed: Jul. 2, 2014

(65) Prior Publication Data

US 2016/0003833 A1   Jan. 7, 2016

(51) Int. Cl.
*G01N 33/564* (2006.01)
*G01N 33/574* (2006.01)
*G01N 33/58* (2006.01)

(52) U.S. Cl.
CPC ..... *G01N 33/57438* (2013.01); *G01N 33/564* (2013.01); *G01N 33/582* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 8,153,421 B2 | 4/2012 | Maitland et al. | |
| 8,512,963 B2 | 8/2013 | Graham et al. | |
| 2004/0059519 A1 | 3/2004 | Chandler et al. | |
| 2004/0241653 A1 | 12/2004 | Feinstein et al. | |
| 2005/0136489 A1 | 6/2005 | Tseng et al. | |
| 2006/0280738 A1* | 12/2006 | Tedder | A61K 38/13 424/141.1 |
| 2011/0306513 A1 | 12/2011 | Song et al. | |
| 2012/0003639 A1 | 1/2012 | Kerlikowske et al. | |
| 2012/0040861 A1 | 2/2012 | Williams et al. | |
| 2012/0067742 A1 | 3/2012 | Lee et al. | |
| 2012/0077682 A1 | 3/2012 | Bowcock et al. | |
| 2012/0077688 A1 | 3/2012 | Bergo et al. | |
| 2013/0183737 A1 | 7/2013 | Borlak | |

FOREIGN PATENT DOCUMENTS

| | | |
|---|---|---|
| EP | 2620772 A1 | 7/2013 |
| KR | 1020110129508 A | 12/2011 |
| WO | 2005016126 A2 | 2/2005 |
| WO | 2010081240 A1 | 7/2010 |
| WO | 2011162904 A2 | 12/2011 |
| WO | 2012004565 A1 | 1/2012 |
| WO | 2012019300 A1 | 2/2012 |
| WO | 2012021795 A2 | 2/2012 |
| WO | 2012021887 A2 | 2/2012 |
| WO | 2012040614 A1 | 3/2012 |
| WO | 2012061904 A1 | 5/2012 |
| WO | 2012115885 A1 | 8/2012 |
| WO | 2013116331 A1 | 8/2013 |
| WO | 2014018903 A1 | 1/2014 |
| WO | WO2015049289 * | 4/2014 |

OTHER PUBLICATIONS

Dudas et al, Cancer Biomark 6:257-270, 2010.*
PE conjugation of secondary antibodies (reference in1986 cited by online publication, down load 2016).*
Karen S. Anderson et al., "The sentinel within: exploiting the immune system for cancer biomarkers", J Proteome Res., 2005, 4(4), p. 1123-1133.
Nilanjana Bose et al., "The clinical utility of anti-chromatin antibodies as measured by BioPlex 2200 in the diagnosis of systemic lupus erythematosus versus other rheumatic diseases", Int J Clin Exp Med, 2012, 5(4), p. 316-320.
Jian Guo Chen et al., "Liver cancer epidemic in China: Past, present and future", Seminars in Cancer Biology, 2011, 21(1), p. 59-69.
Colombo M et al., "Hepatocellular carcinoma in Italian patients with cirrhosis", The New England Journal of Medicine, 1991, 325(10), p. 675-680.
Susan Costantini et al., "Cytokinome Profile of Patients with Type 2 Diabetes and/ or Chronic Hepatitis C Infection", PLoS One, 2012, 7(6), p. 1-12.
Liping Dai et al., "Autoantibodies to tumor-associated antigens as biomarkers in human hepatocellular carcinoma (HCC)", Experimental Hematology & Oncology 2013, 2 (1), p. 1-17.
Liping Dai et al., "Using immunomic approach to enhance tumor-associated autoantibody detection in diagnosis of hepatocellular carcinoma", Clinical Immunology, 2014, 152(1-2), p. 127-139.
Vaios Karanikas et al., "Anti-survivin antibody responses in lung cancer", Cancer Letters, 2009, 282(2), p. 159-166.

(Continued)

Primary Examiner — Lei Yao
(74) Attorney, Agent, or Firm — Hogan Lovells US LLP

(57) ABSTRACT

Cells within liver tumour mass comprise a unique set of proteins/tumour antigens when compared to the normal liver tissues epithelial cells juxtaposed to the tumour. The presence of tumour antigens couples the production of autoantibodies against these tumour antigens. The present invention relates to the identification and elucidation of a protein set that can act as a novel marker set for liver cancer diagnosis and prognosis. Specifically, it relates to a kit that enables diagnostic and prognostic measurement of autoantibodies in serum of liver cancer patients. The present invention provides a non-invasive, specific, sensitive, and cost effective detection and quantification method by evaluating a set of validated liver cancer proteins/tumour antigens, which includes Bmi-1, VCC1, SUMO-4, RhoA, TXN, ET-1, UBE2C, HDGF2, FGF21, LECT2, SOD1, STMN4, Midkine, IL-17A or IL26, to complement the conventional diagnostic methods.

2 Claims, 17 Drawing Sheets

(56) References Cited

OTHER PUBLICATIONS

Brian Nolen et al., "Aberrant tumor-associated antigen autoantibody profiles in healthy controls detected by multiplex bead-based immunoassay", Journal of Immunological Methods, 2009, 344(2), p. 116-120.

Heather P. Ostendorff et al., "Multiplexed VeraCode bead-based serological immunoassay for colorectal cancer", Journal of Immunological Methods, 2013, 400-401, p. 58-69.

Kenkichi Masutomi et al., "Identi®cation of serum anti-human telomerase reverse transcriptase (hTERT) auto-antibodies during progression to hepatocellular carcinoma", Oncogene, 2002, 21(38), p. 5946-5950.

Niroshan Ramachandran1 et al., "Tracking Humoral Responses Using Self Assembling Protein Microarrays", Proteomics Clin Appl., 2008, 2(10-11)p. 1518-1527.

Dushyant V. Sahani et al., "Imaging the liver", The Oncologist, 2004, 9(4), p. 385-397.

Yu-Qian Wang et al., "Correlation Between Auto-antibodies to Survivin and MUC1 Variable Number Tandem Repeats in Colorectal Cancer", Asian Pacific Journal of Cancer Prevention, 2012, 13(11), p. 5557-5562.

Jessica Wong et al., "Rapid Detection of Antibodies in Sera Using Multiplexed Self-Assembling Bead Arrays", J Immunol Methods, 2009, 350(1-2), p. 171-182.

Yan Tang et al., "Detection of Circulating Anti-Mucin 1 (MUC1) Antibodies in Breast Tumor Patients by Indirect Enzyme-Linked Immunosorbent Assay Using a Recombinant MUC1 Protein Containing Six Tandem Repeats and Expressed in *Escherichia coli*", Clinical and Vaccine Immunology, 2010, 17(12), p. 1903-1908.

Salama et al., "Chemiluminiscent optical fiber immunosensor for detection of autoantibodies to ovarian and breast cancer-associated antigens", Biosensors and Bioelectronics, 22 (2007), 1508-1516.

International Search Report and Written Opinion dated Feb. 19, 2015 for corresponding PCT application PCT/US14/49038.

\* cited by examiner

| Spot | Protein | MW (kD) |
|---|---|---|
| 1 | Bmi1 | 37 |
| 2 | VCC1 | 13.6 |
| 3 | SUMO-4 | 11 |
| 4 | RhoA | 22 |
| 5 | TXN | 12 |
| 6 | ET-1 | 24 |
| 7 | UBE2C | 20 |
| 8 | HDGF2 | 74 |
| 9 | FGF21 | 20 |
| 10 | LECT2 | 16 |
| 11 | SOD1 | 16 |
| 12 | STMN4 | 22 |
| 13 | Midkine | 19 |
| 14 | IL-17A | 17.5 |
| 15 | IL-26 | 20 |

FIG. 2

SEQUENCE LISTING

```
<160> NUMBER OF SEQ ID NOS: 15

<210> SEQ ID NO 1
<211> LENGTH: 326
<212> TYPE: PRT
<213> ORGANISM: Homo sapiens

<400> SEQUENCE: 1

Met His Arg Thr Thr Arg Ile Lys Ile Thr Glu Leu Asn Pro His Leu
1               5                   10                  15

Met Cys Val Leu Cys Gly Gly Tyr Phe Ile Asp Ala Thr Thr Ile Ile
            20                  25                  30

Glu Cys Leu His Ser Phe Cys Lys Thr Cys Ile Val Arg Tyr Leu Glu
        35                  40                  45

Thr Ser Lys Tyr Cys Pro Ile Cys Asp Val Gln Val His Lys Thr Arg
    50                  55                  60

Pro Leu Leu Asn Ile Arg Ser Asp Lys Thr Leu Gln Asp Ile Val Tyr
65                  70                  75                  80

Lys Leu Val Pro Gly Leu Phe Lys Asn Glu Met Lys Arg Arg Arg Asp
                85                  90                  95

Phe Tyr Ala Ala His Pro Ser Ala Asp Ala Ala Asn Gly Ser Asn Glu
            100                 105                 110

Asp Arg Gly Glu Val Ala Asp Glu Asp Lys Arg Ile Ile Thr Asp Asp
        115                 120                 125

Glu Ile Ile Ser Leu Ser Ile Glu Phe Phe Asp Gln Asn Arg Leu Asp
    130                 135                 140

Arg Lys Val Asn Lys Asp Lys Glu Lys Ser Lys Glu Glu Val Asn Asp
145                 150                 155                 160

Lys Arg Tyr Leu Arg Cys Pro Ala Ala Met Thr Val Met His Leu Arg
                165                 170                 175

Lys Phe Leu Arg Ser Lys Met Asp Ile Pro Asn Thr Phe Gln Ile Asp
            180                 185                 190

Val Met Tyr Glu Glu Glu Pro Leu Lys Asp Tyr Tyr Thr Leu Met Asp
        195                 200                 205

Ile Ala Tyr Ile Tyr Thr Trp Arg Arg Asn Gly Pro Leu Pro Leu Lys
    210                 215                 220
```

```
Tyr Arg Val Arg Pro Thr Cys Lys Arg Met Lys Ile Ser His Gln Arg
225                 230                 235                 240

Asp Gly Leu Thr Asn Ala Gly Glu Leu Glu Ser Asp Ser Gly Ser Asp
                245                 250                 255

Lys Ala Asn Ser Pro Ala Gly Gly Ile Pro Ser Thr Ser Ser Cys Leu
                260                 265                 270

Pro Ser Pro Ser Thr Pro Val Gln Ser Pro His Pro Gln Phe Pro His
            275                 280                 285

Ile Ser Ser Thr Met Asn Gly Thr Ser Asn Ser Pro Ser Gly Asn His
            290                 295                 300

Gln Ser Ser Phe Ala Asn Arg Pro Arg Lys Ser Ser Val Asn Gly Ser
305                 310                 315                 320

Ser Ala Thr Ser Ser Gly
                325

<210> SEQ ID NO 2
<211> LENGTH: 119
<212> TYPE: PRT
<213> ORGANISM: Homo sapiens

<400> SEQUENCE: 2

Met Lys Val Leu Ile Ser Ser Leu Leu Leu Leu Pro Leu Met Leu Leu
1               5                   10                  15

Met Ser Met Val Ser Ser Leu Asn Pro Gly Val Ala Arg Gly His
            20                  25                  30

Arg Asp Arg Gly Gln Ala Ser Arg Arg Trp Leu Gln Glu Gly Gly Gln
            35                  40                  45

Glu Cys Glu Cys Lys Asp Trp Phe Leu Arg Ala Pro Arg Arg Lys Phe
    50                  55                  60

Met Thr Val Ser Gly Leu Pro Lys Lys Gln Cys Pro Cys Asp His Phe
65                  70                  75                  80

Lys Gly Asn Val Lys Lys Thr Arg His Gln Arg His His Arg Lys Pro
                85                  90                  95

Asn Lys His Ser Arg Ala Cys Gln Gln Phe Leu Lys Gln Cys Gln Leu
            100                 105                 110

Arg Ser Phe Ala Leu Pro Leu
            115

<210> SEQ ID NO 3
<211> LENGTH: 95
<212> TYPE: PRT
<213> ORGANISM: Homo sapiens

<400> SEQUENCE: 3

Met Ala Asn Glu Lys Pro Thr Glu Glu Val Lys Thr Glu Asn Asn Asn
1               5                   10                  15

His Ile Asn Leu Lys Val Ala Gly Gln Asp Gly Ser Val Val Gln Phe
            20                  25                  30

Lys Ile Lys Arg Gln Thr Pro Leu Ser Lys Leu Met Lys Ala Tyr Cys
            35                  40                  45

Glu Pro Arg Gly Leu Ser Val Lys Gln Ile Arg Phe Arg Phe Gly Gly
    50                  55                  60

Gln Pro Ile Ser Gly Thr Asp Lys Pro Ala Gln Leu Glu Met Glu Asp
65                  70                  75                  80

Glu Asp Thr Ile Asp Val Phe Gln Gln Pro Thr Gly Gly Val Tyr
                85                  90                  95
```

```
<210> SEQ ID NO 4
<211> LENGTH: 193
<212> TYPE: PRT
<213> ORGANISM: Homo sapiens

<400> SEQUENCE: 4

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Ser Gly Cys Leu Val
                180                 185                 190
Leu

<210> SEQ ID NO 5
<211> LENGTH: 105
<212> TYPE: PRT
<213> ORGANISM: Homo sapiens

<400> SEQUENCE: 5

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 6
<211> LENGTH: 212
<212> TYPE: PRT
```

<213> ORGANISM: Homo sapiens

<400> SEQUENCE: 6

Met Asp Tyr Leu Leu Met Ile Phe Ser Leu Phe Val Ala Cys Gln
1               5                   10                  15

Gly Ala Pro Glu Thr Ala Val Leu Gly Ala Glu Leu Ser Ala Val Gly
                20                  25                  30

Glu Asn Gly Gly Glu Lys Pro Thr Pro Ser Pro Pro Trp Arg Leu Arg
            35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu His Leu Arg Gln
                165                 170                 175

Thr Arg Ser Glu Thr Met Arg Asn Ser Val Lys Ser Ser Phe His Asp
            180                 185                 190

Pro Lys Leu Lys Gly Asn Pro Ser Arg Glu Arg Tyr Val Thr His Asn
        195                 200                 205

Arg Ala His Trp
    210

<210> SEQ ID NO 7
<211> LENGTH: 179
<212> TYPE: PRT
<213> ORGANISM: Homo sapiens

<400> SEQUENCE: 7

Met Ala Ser Gln Asn Arg Asp Pro Ala Ala Thr Ser Val Ala Ala Ala
1               5                   10                  15

Arg Lys Gly Ala Glu Pro Ser Gly Gly Ala Ala Arg Gly Pro Val Gly
                20                  25                  30

Lys Arg Leu Gln Gln Glu Leu Met Thr Leu Met Met Ser Gly Asp Lys
            35                  40                  45

Gly Ile Ser Ala Phe Pro Glu Ser Asp Asn Leu Phe Lys Trp Val Gly
        50                  55                  60

Thr Ile His Gly Ala Ala Gly Thr Val Tyr Glu Asp Leu Arg Tyr Lys
65                  70                  75                  80

Leu Ser Leu Glu Phe Pro Ser Gly Tyr Pro Tyr Asn Ala Pro Thr Val
                85                  90                  95

Lys Phe Leu Thr Pro Cys Tyr His Pro Asn Val Asp Thr Gln Gly Asn
            100                 105                 110

Ile Cys Leu Asp Ile Leu Lys Glu Lys Trp Ser Ala Leu Tyr Asp Val
        115                 120                 125

Arg Thr Ile Leu Leu Ser Ile Gln Ser Leu Leu Gly Glu Pro Asn Ile

```
                130                 135                 140
Asp Ser Pro Leu Asn Thr His Ala Ala Glu Leu Trp Lys Asn Pro Thr
145                 150                 155                 160

Ala Phe Lys Lys Tyr Leu Gln Glu Thr Tyr Ser Lys Gln Val Thr Ser
                165                 170                 175

Gln Glu Pro

<210> SEQ ID NO 8
<211> LENGTH: 203
<212> TYPE: PRT
<213> ORGANISM: Homo sapiens

<400> SEQUENCE: 8

Met Ala Arg Pro Arg Pro Arg Glu Tyr Lys Ala Gly Asp Leu Val Phe
1               5                   10                  15

Ala Lys Met Lys Gly Tyr Pro His Trp Pro Ala Arg Ile Asp Glu Leu
                20                  25                  30

Pro Glu Gly Ala Val Lys Pro Ala Asn Lys Tyr Pro Ile Phe Phe
            35                  40                  45

Phe Gly Thr His Glu Thr Ala Phe Leu Gly Pro Lys Asp Leu Phe Pro
        50                  55                  60

Tyr Lys Glu Tyr Lys Asp Lys Phe Gly Lys Ser Asn Lys Arg Lys Gly
65                  70                  75                  80

Phe Asn Glu Gly Leu Trp Glu Ile Glu Asn Asn Pro Gly Val Lys Phe
                85                  90                  95

Thr Gly Tyr Gln Ala Ile Gln Gln Gln Ser Ser Ser Thr Glu Gly
            100                 105                 110

Glu Gly Gly Asn Thr Ala Asp Ala Ser Ser Glu Glu Glu Gly Asp Arg
        115                 120                 125

Val Glu Glu Asp Gly Lys Gly Lys Arg Lys Asn Glu Lys Ala Gly Ser
    130                 135                 140

Lys Arg Lys Lys Ser Tyr Thr Ser Lys Lys Ser Ser Gln Ser Arg
145                 150                 155                 160

Lys Ser Pro Gly Asp Glu Asp Lys Asp Cys Lys Glu Glu Glu Asn
                165                 170                 175

Lys Ser Ser Ser Glu Gly Gly Asp Ala Gly Asn Asp Thr Arg Asn Thr
            180                 185                 190

Thr Ser Asp Leu Gln Lys Thr Ser Glu Gly Thr
        195                 200

<210> SEQ ID NO 9
<211> LENGTH: 209
<212> TYPE: PRT
<213> ORGANISM: Homo sapiens

<400> SEQUENCE: 9

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80
```

```
Leu Gln Leu Lys Ala Leu Lys Pro Gly Val Ile Gln Ile Leu Gly Val
            85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
            165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser
```

<210> SEQ ID NO 10
<211> LENGTH: 151
<212> TYPE: PRT
<213> ORGANISM: Homo sapiens

<400> SEQUENCE: 10

```
Met Phe Ser Thr Lys Ala Leu Leu Ala Gly Leu Ile Ser Thr Ala
1               5                   10                  15

Leu Ala Gly Pro Trp Ala Asn Ile Cys Ala Gly Lys Ser Ser Asn Glu
            20                  25                  30

Ile Arg Thr Cys Asp Arg His Gly Cys Gly Gln Tyr Ser Ala Gln Arg
            35                  40                  45

Ser Gln Arg Pro His Gln Gly Val Asp Val Leu Cys Ser Ala Gly Ser
        50                  55                  60

Thr Val Tyr Ala Pro Phe Thr Gly Met Ile Val Gly Gln Glu Lys Pro
65                  70                  75                  80

Tyr Gln Asn Lys Asn Ala Ile Asn Asn Gly Val Arg Ile Ser Gly Arg
            85                  90                  95

Gly Phe Cys Val Lys Met Phe Tyr Ile Lys Pro Ile Lys Tyr Lys Gly
            100                 105                 110

Pro Ile Lys Lys Gly Glu Lys Leu Gly Thr Leu Leu Pro Leu Gln Lys
            115                 120                 125

Val Tyr Pro Gly Ile Gln Ser His Val His Ile Glu Asn Cys Asp Ser
130                 135                 140

Ser Asp Pro Thr Ala Tyr Leu
145                 150
```

<210> SEQ ID NO 11
<211> LENGTH: 153
<212> TYPE: PRT
<213> ORGANISM: Homo sapiens

<400> SEQUENCE: 11

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30
```

-continued

```
Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
 50                  55                  60

Phe Asn Pro Leu Ser Arg Lys His Gly Pro Lys Asp Glu Glu Arg
 65                  70                  75                  80

His Val Gly Asp Leu Gly Asn Val Thr Ala Asp Lys Asp Gly Val Ala
                85                  90                  95

Asp Val Ser Ile Glu Asp Val Ile Leu Ser Gly Asp His Cys Ile
                100                 105                 110

Ile Gly Arg Thr Leu Val Val His Glu Lys Ala Asp Asp Leu Gly Lys
            115                 120                 125

Gly Gly Asn Glu Glu Ser Thr Lys Thr Gly Asn Ala Gly Ser Arg Leu
 130                 135                 140

Ala Cys Gly Val Ile Gly Ile Ala Gln
145                 150

<210> SEQ ID NO 12
<211> LENGTH: 189
<212> TYPE: PRT
<213> ORGANISM: Homo sapiens

<400> SEQUENCE: 12

Met Thr Leu Ala Ala Tyr Lys Glu Lys Met Lys Glu Leu Pro Leu Val
 1               5                   10                  15

Ser Leu Phe Cys Ser Cys Phe Leu Ala Asp Pro Leu Asn Lys Ser Ser
                20                  25                  30

Tyr Lys Tyr Glu Ala Asp Thr Val Asp Leu Asn Trp Cys Val Ile Ser
            35                  40                  45

Asp Met Glu Val Ile Glu Leu Asn Lys Cys Thr Ser Gly Gln Ser Phe
 50                  55                  60

Glu Val Ile Leu Lys Pro Pro Ser Phe Asp Gly Val Pro Glu Phe Asn
 65                  70                  75                  80

Ala Ser Leu Pro Arg Arg Arg Asp Pro Ser Leu Glu Glu Ile Gln Lys
                85                  90                  95

Lys Leu Glu Ala Ala Glu Glu Arg Arg Lys Tyr Gln Glu Ala Glu Leu
                100                 105                 110

Leu Lys His Leu Ala Glu Lys Arg Glu His Glu Arg Glu Val Ile Gln
            115                 120                 125

Lys Ala Ile Glu Glu Asn Asn Asn Phe Ile Lys Met Ala Lys Glu Lys
 130                 135                 140

Leu Ala Gln Lys Met Glu Ser Asn Lys Glu Asn Arg Glu Ala His Leu
145                 150                 155                 160

Ala Ala Met Leu Glu Arg Leu Gln Glu Lys Asp Lys His Ala Glu Glu
                165                 170                 175

Val Arg Lys Asn Lys Glu Leu Lys Glu Glu Ala Ser Arg
                180                 185

<210> SEQ ID NO 13
<211> LENGTH: 143
<212> TYPE: PRT
<213> ORGANISM: Homo sapiens

<400> SEQUENCE: 13

Met Gln His Arg Gly Phe Leu Leu Leu Thr Leu Leu Ala Leu Leu Ala
 1               5                   10                  15
```

```
Leu Thr Ser Ala Val Ala Lys Lys Asp Lys Val Lys Gly Gly
            20                  25                  30

Pro Gly Ser Glu Cys Ala Glu Trp Ala Trp Gly Pro Cys Thr Pro Ser
        35                  40                  45

Ser Lys Asp Cys Gly Val Gly Phe Arg Glu Gly Thr Cys Gly Ala Gln
    50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
            100                 105                 110

Asn Ala Gln Cys Gln Glu Thr Ile Arg Val Thr Lys Pro Cys Thr Pro
        115                 120                 125

Lys Thr Lys Ala Lys Ala Lys Ala Lys Lys Gly Lys Gly Lys Asp
    130                 135                 140
```

<210> SEQ ID NO 14
<211> LENGTH: 155
<212> TYPE: PRT
<213> ORGANISM: Homo sapiens

<400> SEQUENCE: 14

```
Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155
```

<210> SEQ ID NO 15
<211> LENGTH: 171
<212> TYPE: PRT
<213> ORGANISM: Homo sapiens

<400> SEQUENCE: 15

```
Met Leu Val Asn Phe Ile Leu Arg Cys Gly Leu Leu Leu Val Thr Leu
1               5                   10                  15

Ser Leu Ala Ile Ala Lys His Lys Gln Ser Ser Phe Thr Lys Ser Cys
            20                  25                  30

Tyr Pro Arg Gly Thr Leu Ser Gln Ala Val Asp Ala Leu Tyr Ile Lys
        35                  40                  45
```

-continued

```
Ala Ala Trp Leu Lys Ala Thr Ile Pro Glu Asp Arg Ile Lys Asn Ile
    50              55                  60
Arg Leu Leu Lys Lys Lys Thr Lys Lys Gln Phe Met Lys Asn Cys Gln
65              70                  75                      80
Phe Gln Glu Gln Leu Leu Ser Phe Phe Met Glu Asp Val Phe Gly Gln
                85                  90                  95
Leu Gln Leu Gln Gly Cys Lys Lys Ile Arg Phe Val Glu Asp Phe His
            100             105                 110
Ser Leu Arg Gln Lys Leu Ser His Cys Ile Ser Cys Ala Ser Ser Ala
        115                 120                 125
Arg Glu Met Lys Ser Ile Thr Arg Met Lys Arg Ile Phe Tyr Arg Ile
    130             135                 140
Gly Asn Lys Gly Ile Tyr Lys Ala Ile Ser Glu Leu Asp Ile Leu Leu
145                 150                 155                 160
Ser Trp Ile Lys Lys Leu Leu Glu Ser Ser Gln
                165             170
```

SPECIFIC BIOMARKER SET FOR NON-INVASIVE DIAGNOSIS OF LIVER CANCER

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright© 2014, Vision Global Holdings Limited, All Rights Reserved.

TECHNICAL FIELD

The present invention describes a detection and quantification method for a list of specific and novel Hepatocellular Carcinoma (HCC) tumor biomarkers, by measuring the corresponding auto-antibodies in liver cancer patients' sera. The set of biomarkers comprises Bmi1, VCC1, SUMO-4, RhoA, TXN, ET-1, UBE2C, HDGF2, FGF21, LECT2, SOD1, STMN4, Midkine, IL-17A and IL26. More specifically, this invention further describes a design of a high throughput and sensitive test kit readily available to take patients' peripheral serum samples for detecting liver cancers early and in a non-invasive manner by measuring the auto-antibodies against at least one of the biomarkers selected from the biomarker set. The present invention further allows identification of signature biomarker patterns for staging, as well as the detection of recurrences during a monitoring period of post-chemotherapeutic treatment. The present invention would support automatic data analysis.

BACKGROUND OF INVENTION

Hepatocellular carcinoma (HCC) is the second most prevalent cancer in China, which covers 5.7% of the total population [1]. Most HCC patients have rapid tumor progressing resulting in high mortality rate. In order to improve the overall survival, early diagnosis of the disease becomes essential. Currently, the most common way of detecting HCCs are blood tests that measure level of HCC tumor markers such as alpha fetoprotein (AFP). AFP is a plasma protein produced by yolk sac and liver during the development of fetus serving as a form of serum albumin. In normal condition, AFP level gradually decreases after birth and remain in low level in adults. Increased level of tumor markers indicates probability of liver cancers. However, the major problem of the AFP test is excessive false positive. It is because HCC is not the only cause for the AFP level elevation, but alcoholic hepatitis, chronic hepatitis or cirrhosis also associates with increase of AFP.

Despite AFP test is commonly suggested for diagnosis of liver cancers, its result is not conclusive. Suspected patients will need to go through ultrasound imaging, CT scans or contrast MRI scans for further confirmation. Liver biopsy will be taken to distinguish whether the tumor is benign or malignant. However, conventional detection of HCCs comes with several limitations: (a) About 20% of liver cancers does not produce elevated level of the commonly used HCC tumor markers [2]. (b) Viral cirrhosis produces false positive results on the blood tests [3]. (c) Ultrasound is not able to detect small tumors [4]. (d) CT scans require high radiation dose and are insensitive to tumors less than 1 cm [5]. (e) MRI scans are expensive and the procedure is time consuming. Due to these limitations, there are needs to develop novel biomarkers screen with higher sensitivity and specificity for the purpose of early diagnosis of HCC and/or determining a prognosis of HCC to complement the conventional methods.

HCC tumor cells tend to produce a unique set of proteins when compared to the normal liver epithelial cells juxtaposed to the tumor. Evaluation of validated HCC tumor biomarkers has great potential to facilitate the diagnosis of HCC. However, not all biomarkers themselves can be found in serum or urine for convenient diagnosis. Alternatively, the auto-antibodies which are specifically against the biomarkers provide an opportunity to evaluate the expression of the biomarkers. It has been demonstrated in many cancers that the presence of tumor biomarkers couples the production of auto-antibodies against these tumor antigens [6-8]. Detection on auto-antibodies in patients' sera would allow us to examine the presence of biomarkers more efficiently. Ideally, examination of auto-antibodies from peripheral blood would be a testament for detecting liver cancers early, and in a non-invasive manner One common hurdle hindering clinical use of biomarkers is that they have not been validated after discovery. But once validated, such test would be cost effective and accurate. The design of the prototype also supports high-throughput screening. This may alleviate the cost required for conventional liver cancer diagnosis.

There follows a list of references that are occasionally cited in the specification. Each of the disclosures of these references is incorporated by reference herein in its entirety.

[1] Chen J G, Zhang S W. Liver cancer epidemic in China: past, present and future. Semin Cancer Biol. 2011; 21(1): 59-69

[2] Okuda K, Peters R L. Human alpha-1 fetoprotein. Hepatocellular Carcinoma. 1976:353-67

[3] Lok A S, Lai C L. Alpha-fetoprotein monitoring in Chinese patients with chronic hepatitis E virus infection: role in the early detection of hepatocellular carcinoma. Hepatolog.y 1989; 9:110-115

[4] Colombo M, de Franchis R, Del Ninno E, Sangiovanni A, De Fazio C, Tommasini M, Donato M F, Piva A, Di Carlo V, Dioguardi N. Hepatocellular carcinoma in Italian patients with cirrhosis. N Engl J Med. 1991; 325:675-80

[5] Sahani D V, Kalva S P. Imaging the Liver. The Oncologist. 2004; 9 (4): 385-397

[6] Masutomi K, Kaneko S, Yasukawa M, Arai K, Murakami S, Kobayashi K. Identification of serum anti-human telomerase reverse transcriptase (hTERT) auto-antibodies during progression to hepatocellular carcinoma. Oncogene. 2002 Aug. 29; 21(38):5946-50.

[7] Karanikas V, Khalil S, Kerenidi T, Gourgoulianis K I, Germenis A E. Anti-survivin antibody responses in lung cancer. Cancer Lett. 2009 Sep. 18; 282(2):159-66.

[8] Wang Y Q, Zhang H H, Liu C L, Xia Q, Wu H, Yu X H, Kong W. Correlation between auto-antibodies to survivin and MUC1 variable number tandem repeats in colorectal cancer. Asian Pac J Cancer Prev. 2012; 13(11):5557-62.

SUMMARY OF INVENTION

In the present invention, a detection and quantification method measuring the auto-antibodies against a list of specific tumor biomarker aiming for diagnosing and staging cancers is provided. Comparing to the normal liver epithelial cells, HCC tumor cells tend to produce a unique set of proteins. The evaluation of the unique protein set, biomarkers, will complement the conventional diagnostic methods and facilitate early detection of cancers.

By using a Two-Dimensional/Mass Spectrometry based method, a set of liver cancer biomarkers from paired patients' biopsies (tumor biopsy versus juxtaposed normal tissue) is identified in the present invention comprising Bmi1, VCC1, SUMO-4, RhoA, TXN, ET-1, UBE2C, HDGF2, FGF21, LECT2, SOD1, STMN4, Midkine, IL-17A and IL26.

Specificity and accuracy of this set of liver cancer biomarkers are then validated and taken together for diagnosis of liver cancers. In the present invention, proteins of the listed biomarkers are expressed from cDNA clones, purified and coupled to fluorescent microsphere beads with different emission wavelengths. Auto-antibodies present in patients' sera against the proteins immunologically bind to the protein-bead conjugate. The auto-antibodies subsequently interact with PE-conjugated secondary antibodies. The specific fluorescence signal of the microsphere beads serves as an identifier for the conjugated biomarkers. By measuring the fluorescent intensity given by the PE-conjugated secondary antibodies at the complex, it allows the detection and quantification of the auto-antibodies. Since the auto-antibodies are produced in the patients' sera in proportion to the abundance of the biomarkers at HCC tumor cells, the higher fluorescent intensity resulted from higher concentration of auto-antibodies indicates the higher expression of the corresponding biomarkers. The lowest detection limit of each biomarker to the total serum auto-antibodies is about 0.15 ng/mL.

Comparing to sera from healthy subjects, the level of auto-antibodies against the target biomarkers is at a higher concentration in cancer patient. Moreover, comparing different sera from liver cancer patients at different stages, signature patterns for staging may be generated. Thus, the present invention allows the non-invasive evaluation of the targeted liver cancer biomarker. This enables the detection of HCC at early stages and the identification of signature biomarker patterns for staging, as well as the detection of recurrences during a monitoring period of post-chemotherapeutic treatment.

BRIEF DESCRIPTION OF THE DRAWINGS

Embodiments of the present invention are described in more detail hereinafter with reference to the drawings, in which:

FIG. 2 shows the set of 15 validated liver cancer biomarkers and their corresponding molecular weight targeted and measured in the present invention.

DEFINITIONS

Figure 1:
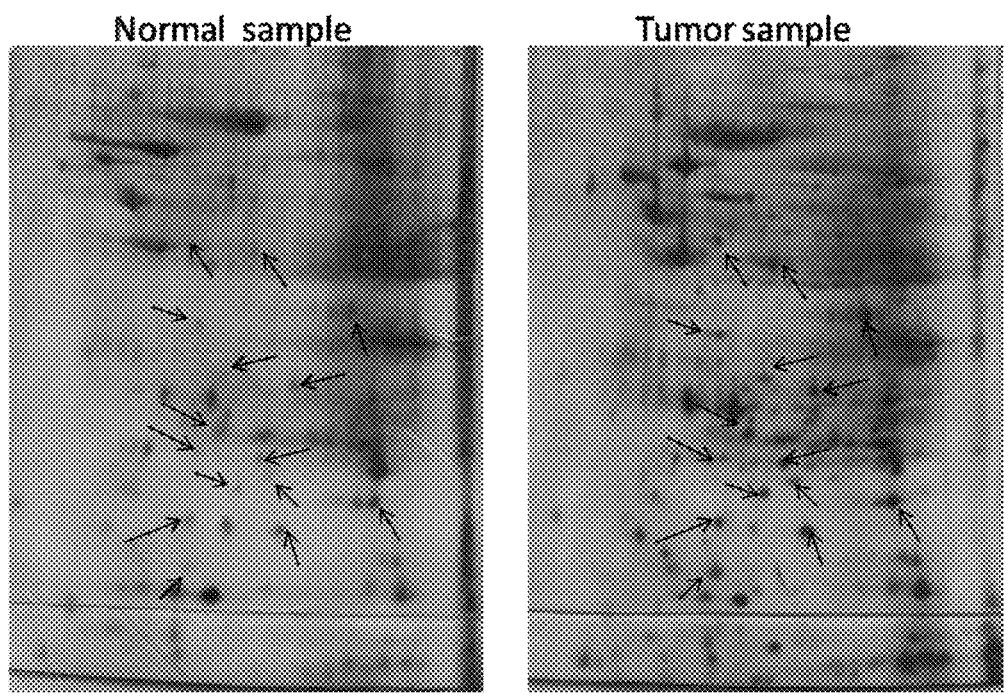
FIG. 1 shows the difference in protein expression pattern between tumor biopsy and juxtaposed normal tissue by two-dimensional/mass spectrometry leading to the identification of 15 specific biomarkers up-regulated in liver cancer; arrows indicate location of spots identified on a 2-D gel of the mass spectrometry.

The term "biomarker" refers to the protein uniquely expressed or up-regulated in the tumor comparing to the normal epithelial cells.

The term "biomarker set" refers to the specific combination of the biomarkers identified from paired patients' biopsies (tumor biopsy versus juxtaposed normal tissue) and is the target of the measurement in the present invention.

The term "auto-antibodies" refers to the anti-bodies produced by the patient body coupling to the expression of the tumor biomarker and it is present in the circulation and can be collected in the peripheral serum.

Bmi1 (Polycomb Ring Finger) is a protein component of a Polycomb Group (PcG) multiprotein PRC1-like complex. It is responsible for maintaining the transcriptionally repressive state of many genes, including Hox genes, throughout development. The regulation is via monoubiquitination of histone H2A 'Lys-119', which modifies histone and remodels chromatin, rendering the expression.

VCC1 or CXCL17 (Chemokine (C-X-C Motif) Ligand 17) has an essential role in angiogenesis and possibly in the development of tumors. It is also suggested that it is a housekeeping chemokine regulating the recruitment of non-activated blood monocytes and immature dendritic cells into tissues. It may also play a role in the innate defense against infections. Malfunction of VCC1 is associated with duodenitis and cholera.

SUMO-4 (Small Ubiquitin-Like Modifier 4) belongs to the family of small ubiquitin-related modifiers and located in the cytoplasm. It covalently attaches to the target protein, IKBA, in order to control its subcellular localization, stability, or activity. This eventually leads to a negative regulation of NF-kappa-B-dependent transcription of the IL12B gene.

RhoA (Ras Homolog Family Member A) regulates the signaling pathway linking plasma membrane receptors to the assembly of focal adhesions and actin stress fibers. It also involves in microtubule-dependent signaling essential during cell cycle cytokinesis, and other signaling pathways involved in stabilization of microtubules and cell migrations and adhesion.

TXN (Thioredoxin) forms homodimer and is involved in redox reactions through the reversible oxidation of its active center dithiol to a disulfide and catalyzes dithiol-disulfide exchange reactions. It has been reported to be associated with breast mucinous carcinoma.

ET-1 (Endothelin 1) is a potent vasoconstrictor produced by vascular endothelial cells. It binds to endothelin receptors widely expressed in all tissues, including non-vascular structure like epithelial cells, glia, and neurons. Apart from the main role in maintenance of vascular tone, it is also suggested to have co-mitogenic activity and potentiate the effects of other growth factors.

UBE2C (Ubiquitin-Conjugating Enzyme E2C) belongs to the family of E2 ubiquitin-conjugating enzyme. This is one of the three enzymes involved in ubiquitination, which is an important cellular mechanism for targeting abnormal proteins for degradation. More specifically, UBE2C is required for the targeted degradation of mitotic cyclins and for cell cycle progression. Thus, it is believed that this protein may be also involved in cancer progression.

HDGF2 is called hepatoma-derived growth factor 2. This protein which is highly expressed in a variety of tumors has been reported to play a pivotal role in the development and progression of several tumors. Although the mechanism is yet to be identified, it is suggested that HDGF2 has mitogenic, angiogenic, neurotrophic and antiapoptotic activity.

FGF21 (Fibroblast Growth Factor 21) is a family member of the FGF family which is involved in vary biological processes including embryonic development, cell growth, morphogenesis, tissue repair, tumor growth and invasion. More specifically, FGF21 stimulates glucose update in differentiated adipocytes via the induction of glucose transporter SLC2A1/GLUT1 expression. It has been found that FGF21 is associated with fatty liver disease.

LECT2 (Leukocyte Cell Derived Chemotaxin 1) is a secretory protein acts as a chemotactic factor to neutrophils and stimulates the growth of chondrocytes and osteoblasts. This protein is associated with acute liver failure.

SOD1 (Superoxide Dismutase 1) is a Cu/Zn-containing antioxidant enzyme responsible for destroying free superoxide radicals into molecular oxygen and hydrogen peroxide in the cytosol, the nucleus, and the intermembrane space of the mitochondria. It is important for maintaining low levels of superoxide in the cytosol, thus protecting the cell from oxidative stress and subsequent cell death.

STMN4 (Stathmin-Like 4) is a small regulatory protein which is believed to have a role in relaying integrating diverse intracellular signaling pathways, which in turn, controls cell proliferation, differentiation and functions. It is also shown that this protein contributes to the control of microtubule dynamics by inhibiting the polymerization of microtubules and/or favoring their depolymerization.

Midkine or NEGF2 (Neurite Growth-Promoting Factor 2) is a secretory growth factor that binds heparin and responsive to retinoic acid. Midkine promotes cell growth, migration and angiogenesis, in particular during tumorigenesis. It has already been demonstrated to be associated with breast adenocarcinoma and soft tissue sarcoma.

IL-17A (Interleukin 17A) is a proinflammatory cytokine produced by the activated T cells. It regulates the activity of NF-kappaB and mitogen-activated protein kinases, stimulates the expression of IL6 and cyclooxygenase-2, and enhances the production of nitric oxide. Several chronic inflammation and sclerosis are usually associated with IL-17A elevation.

IL-26 (Interleukin 26) belongs to the IL-10 cytokine family and is produced by the activated T cells and targets epithelial cells for signal transduction. It binds strongly to glycosaminoglycans such as heparin, heparan sulphate, and dermatan sulfate on cellular surfaces which act similarly to coreceptors in order to enrich IL-26 on the surface of producer and target cells.

Detailed Description of Invention

In the following description, the biomarker/biomarkers, the corresponding embodiments of the detection/validation/identification/quantification methods are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

In the present invention, the set of liver tumor biomarkers for detection and quantification of liver cancer is first identified by two-dimensional/mass spectrometry resolving the difference in the pattern of proteins expression between the paired patients' biopsies (tumor biopsy versus juxtaposed normal tissue) (FIG. 1). The biomarkers are validated by immunohistochemical staining on paraffin-sectioned HCC blocks, and Western Blotting in HCC patients' sera. This results in a finalized list of 15 biomarkers to be evaluated in the present invention for the liver cancer diagnosis purpose (FIG. 2).

Figure 3:
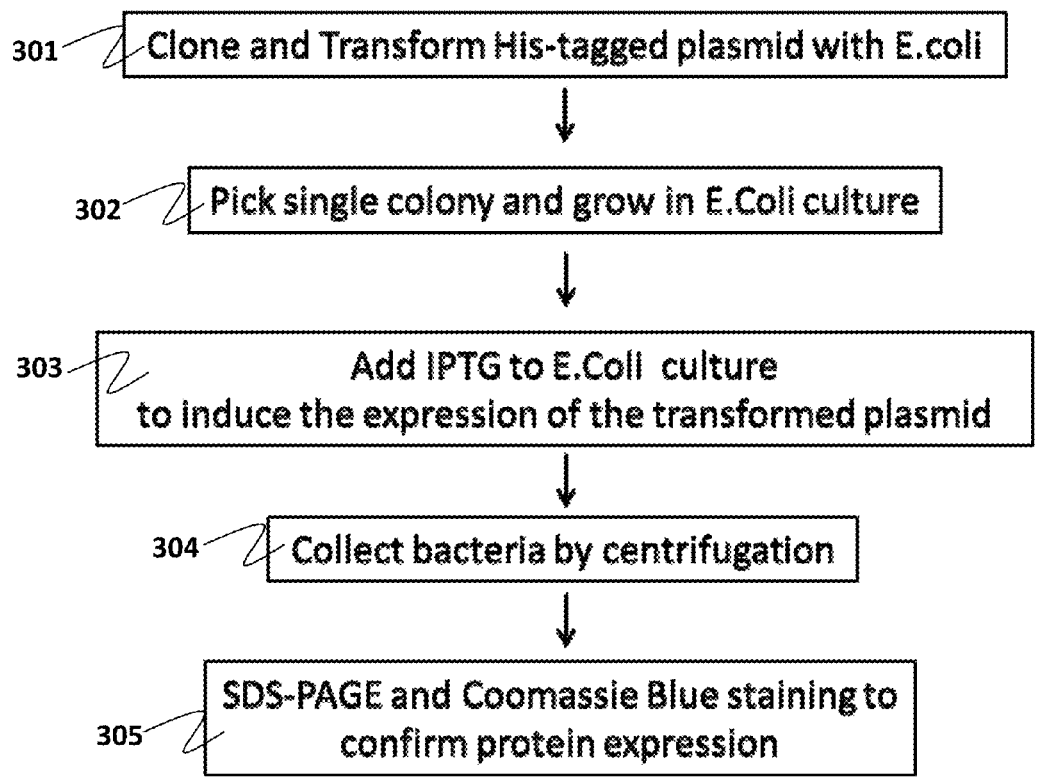
FIG. 3 shows the workflow of expressing the biomarkers from cDNA clones.
Figure 4:
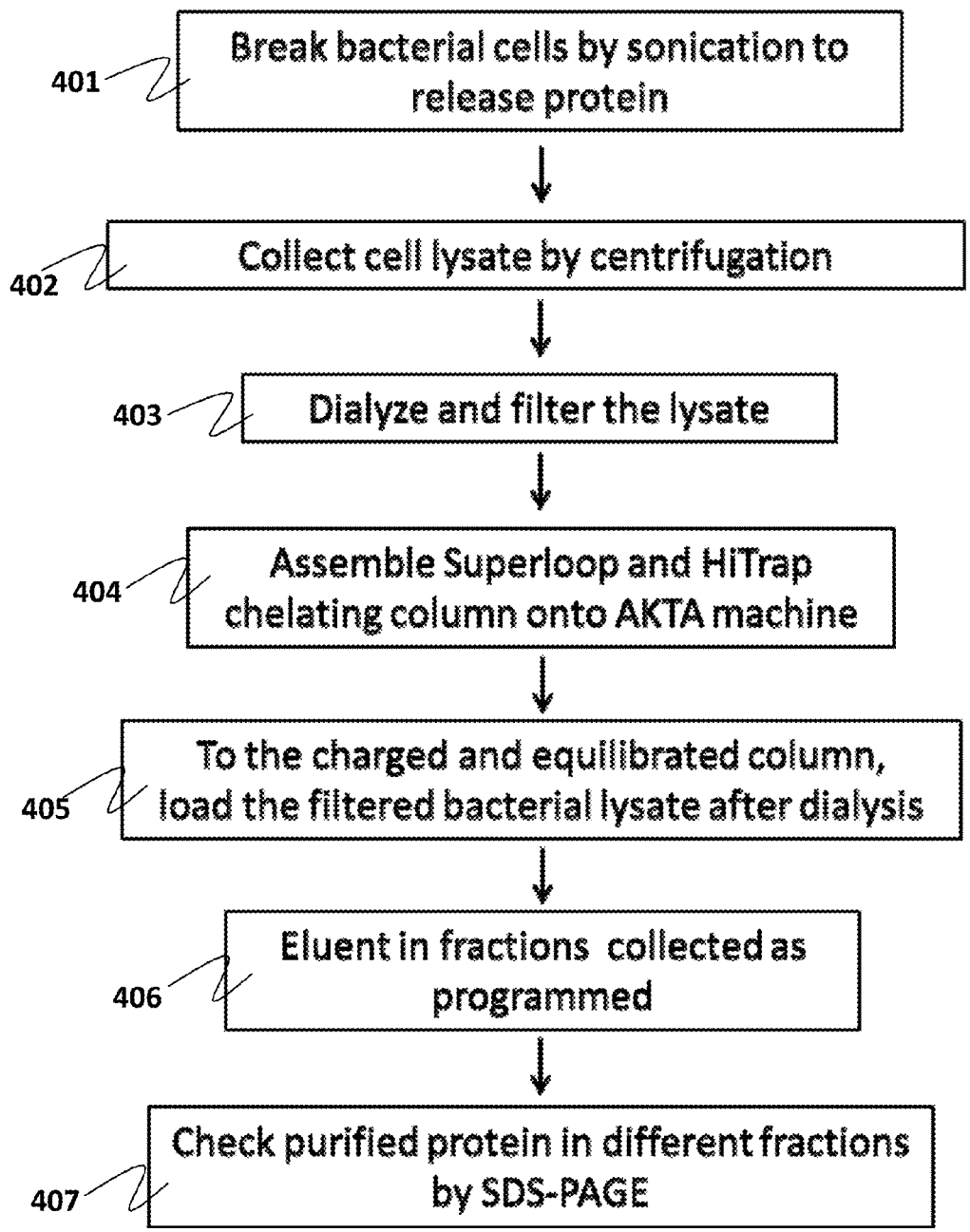
FIG. 4 shows the workflow of purification of the biomarkers expressed from E. coli.
Figure 5:
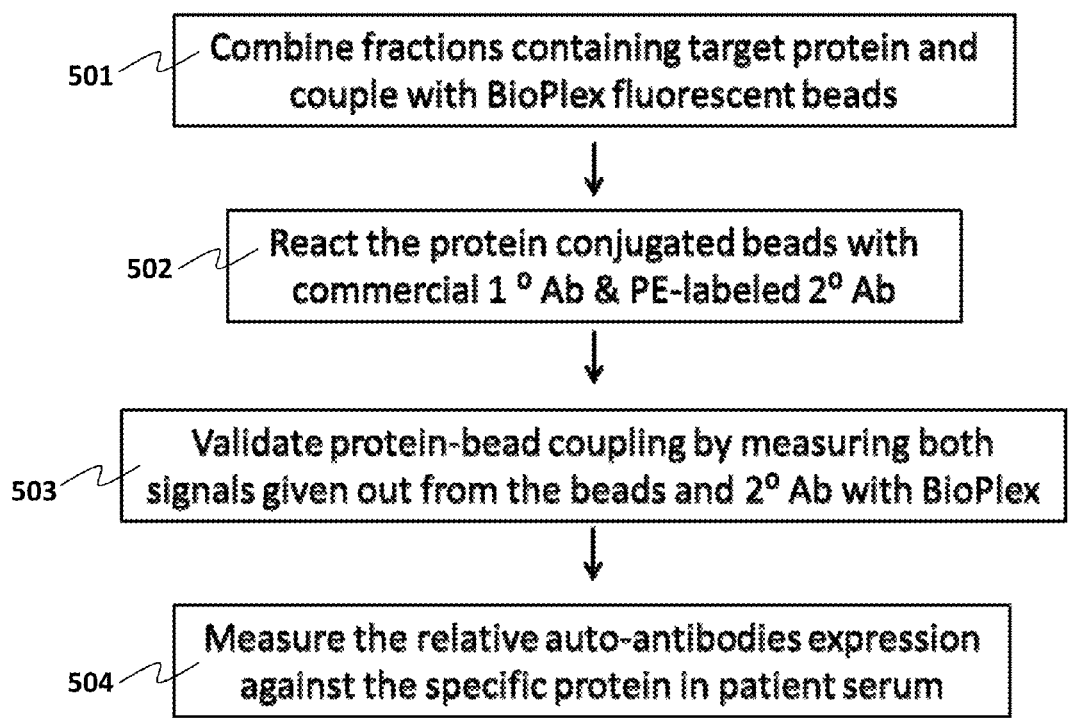
FIG. 5 shows the workflow of measuring the auto-antibodies by BioPlex system.
Figure 6:
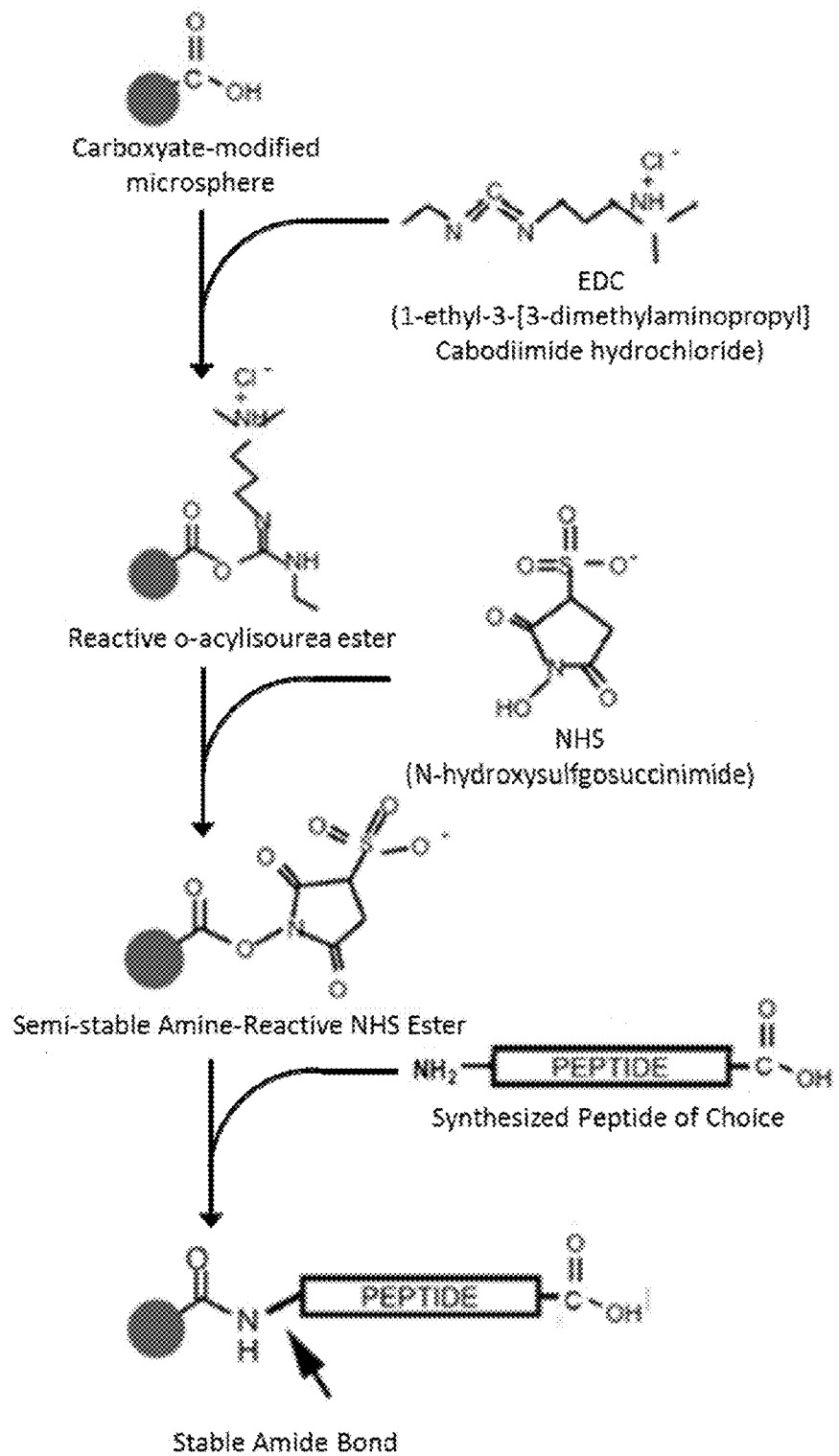
FIG. 6 shows the conjugation of biomarker protein to BioPlex bead.
Figure 7:
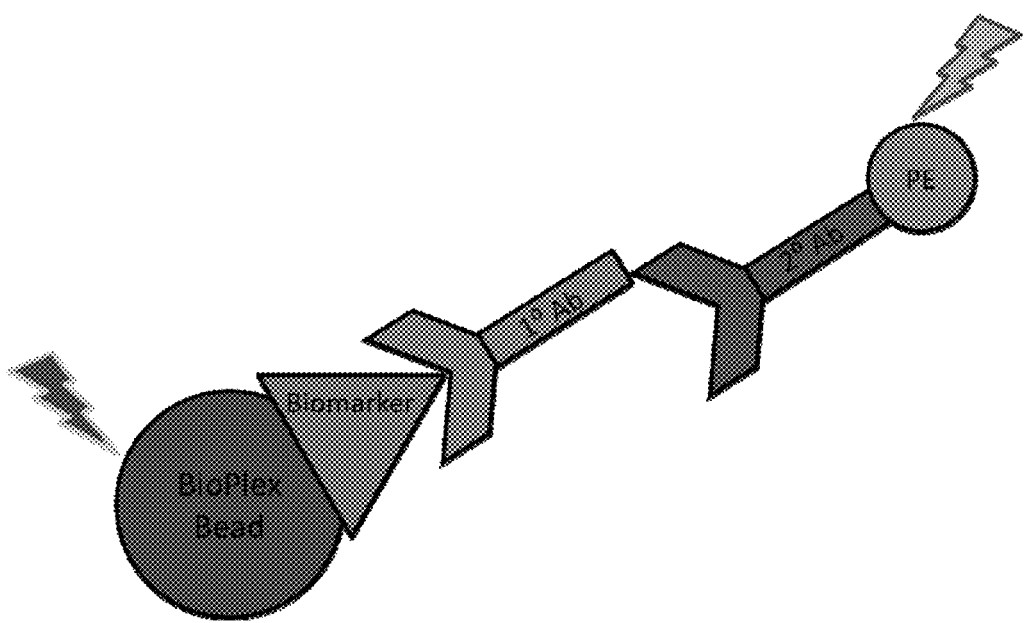
FIG. 7 shows illustration of the complex of biomarker-BioPlex bead conjugate immunoreacting with primary antibody and PE-conjugated secondary antibody.

Based on the amino acid sequences of the targeted biomarkers, commercially synthesized cDNA clones are employed for the expression of the biomarker set (FIG. 3). Proteins expressed from the cDNA clones are then subjected to a series of steps of purifications (FIG. 4). The purified biomarkers are subsequently conjugated via stable amide bonds with BioPlex beads (FIGS. 5, 6), a type of fluorescent microsphere beads and available in a panel which give unique fluorescent signals individually for identification at a multiplex set up. The biomarkers on the beads are recognized by the specific primary antibodies, which are subsequently bound by an anti-human secondary antibody conjugated with PE (FIG. 7). Thus the BioPlex machine simultaneously measures two signals from the complex. The fluorescence given by the BioPlex beads serves as an identifier, while the signal from the PE indicates the presence of the biomarker in the complex. This also helps differentiating the biomarker-bead conjugates bound by the anti-body cascade from those with no immuno-reactivity with antibodies.

Figure 8:
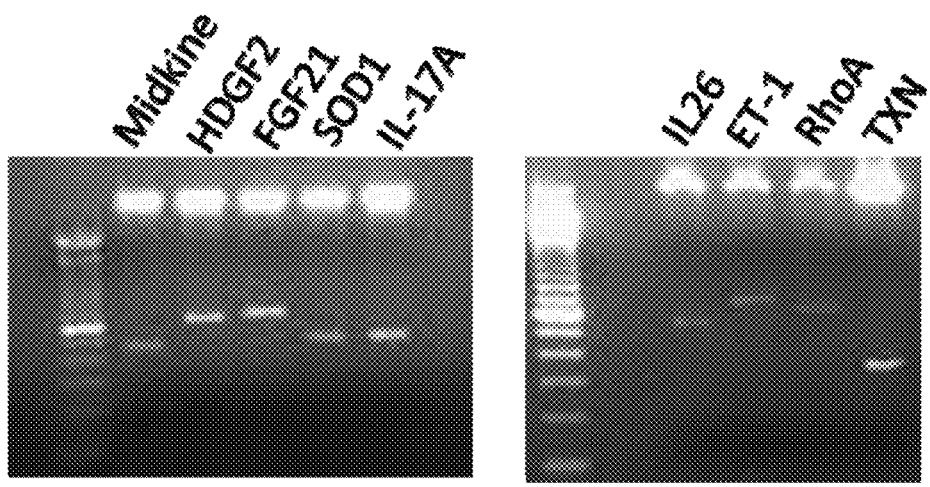
FIG. 8 shows the gel electrophoresis of the DNA insert released from plasmid cut by restriction enzymes HindIII and BamH1.
Figure 9:
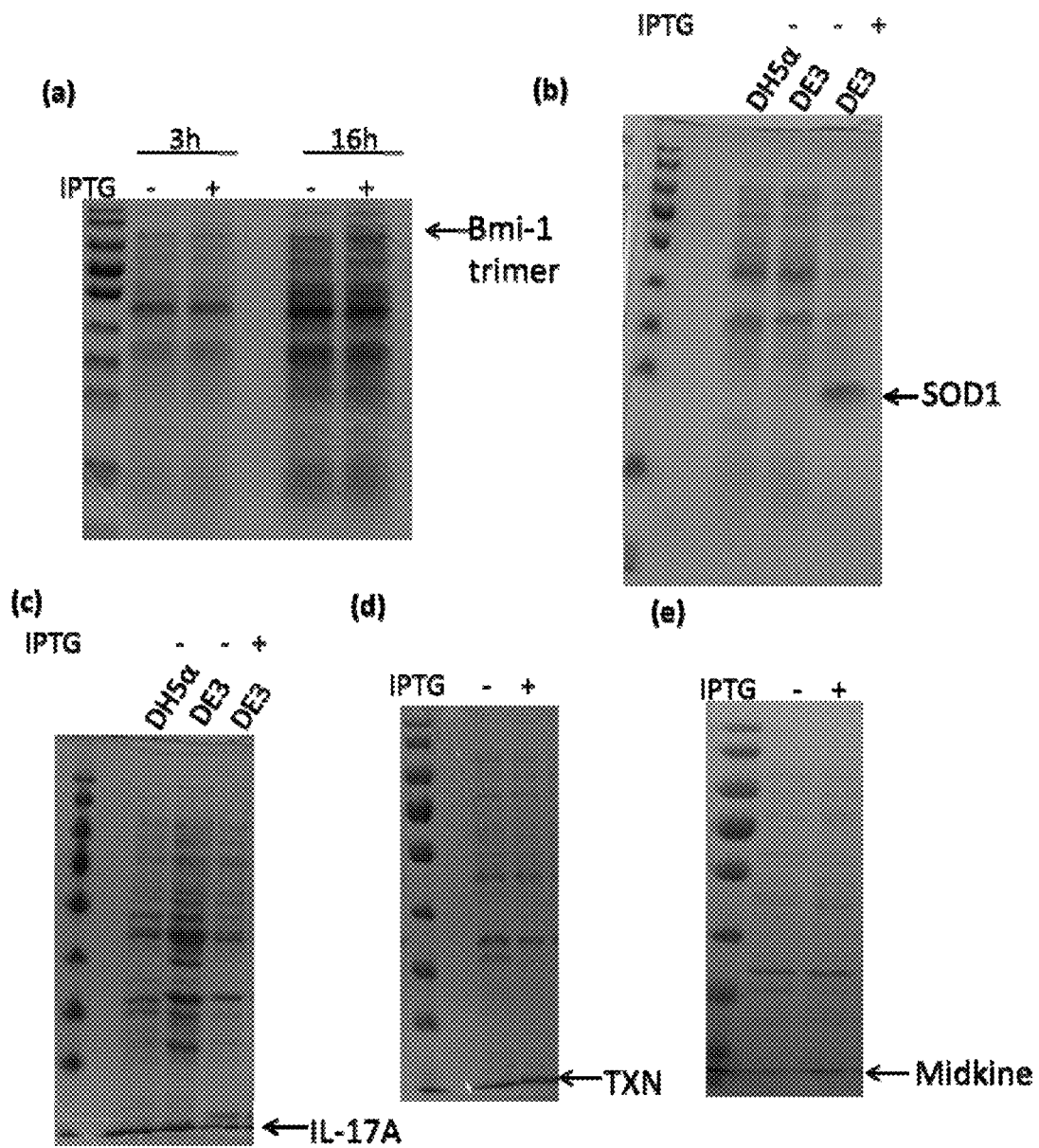
FIG. 9 shows the Coomassie Blue stained SDS-PAGE verifying the IPTG induction of (a) Bmi1, (b) SOD1, (c) IL-17A, (d) TXN and (e) Midkine biomarkers.
Figure 10:
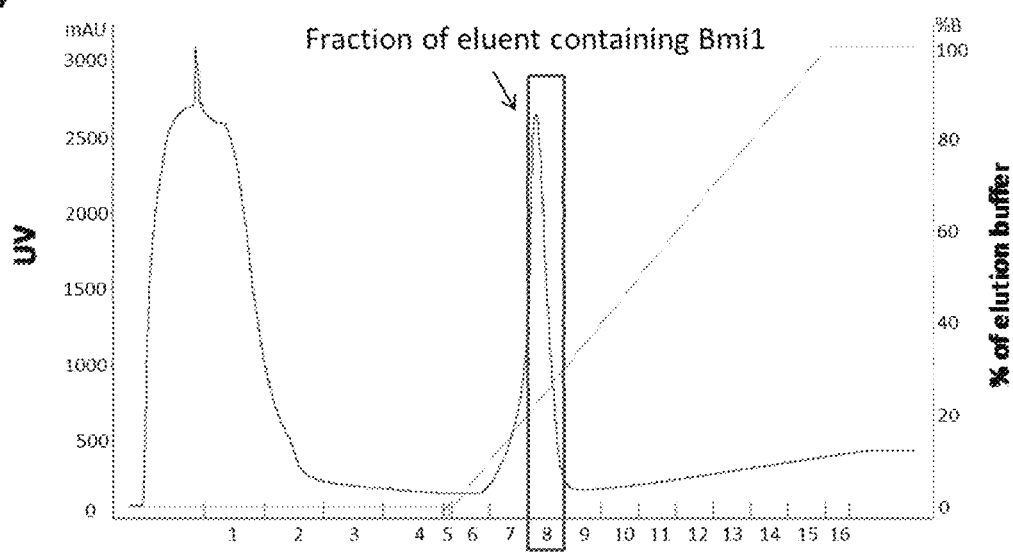
FIG. 10 shows the elution profile of (a) Bmi1, (b) SOD-1 and (e) IL-17A in AKTA.
Figure 10:
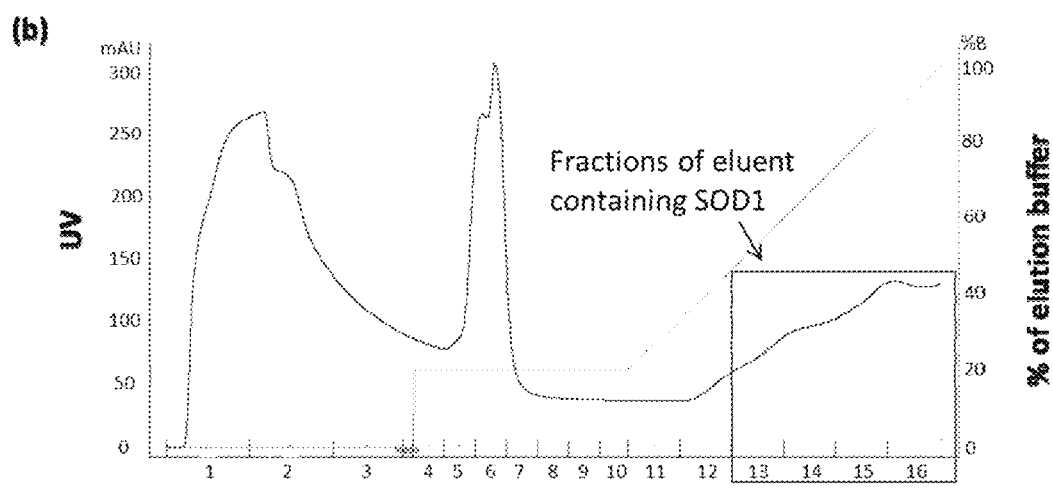
Figure 10:
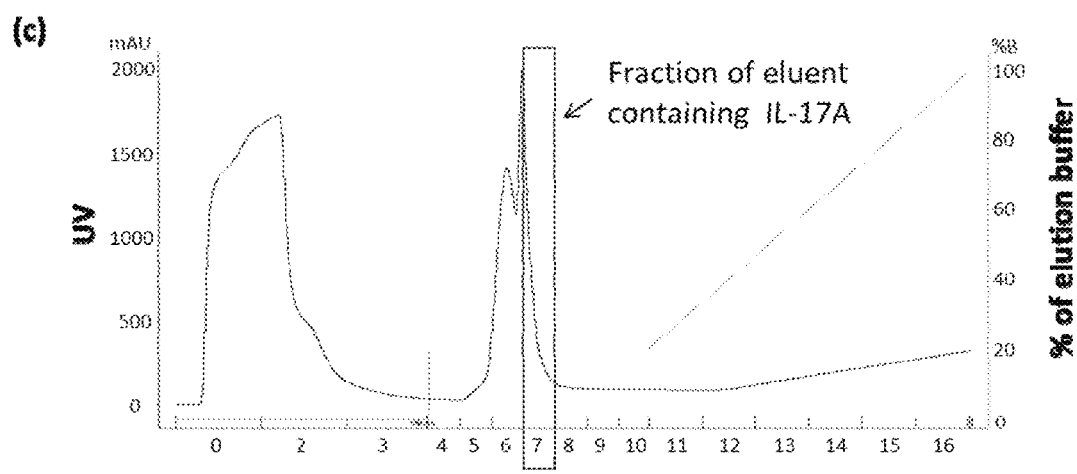
Figure 11:
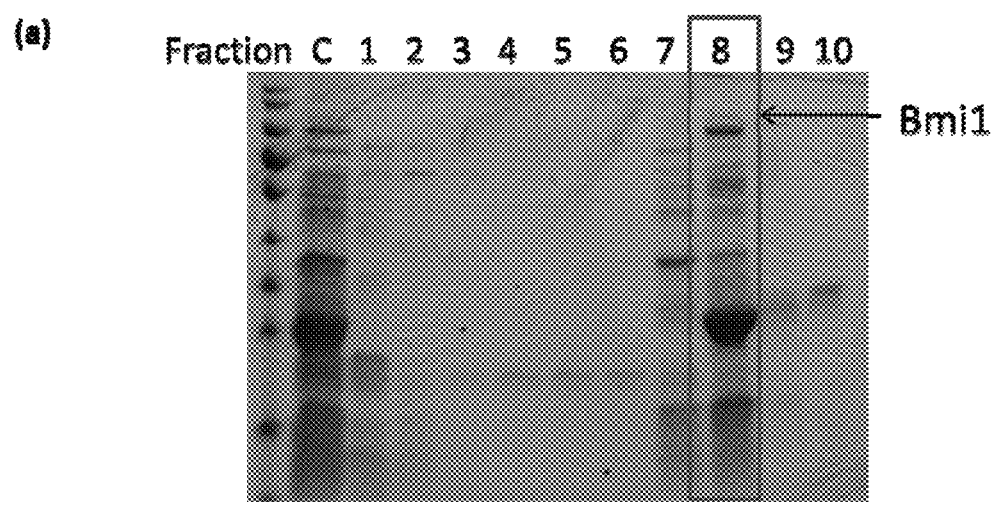
FIG. 11 shows the Coomassie Blue stained SDS-PAGE verifying the purification of His-tagged (a) Bmi1, (b) SOD-1 and (d) IL-17A biomarkers; Fraction A is bacteria without IPTG induction; Fraction B is bacteria with IPTG induction; Fraction C is bacterial lysate.
Figure 11:
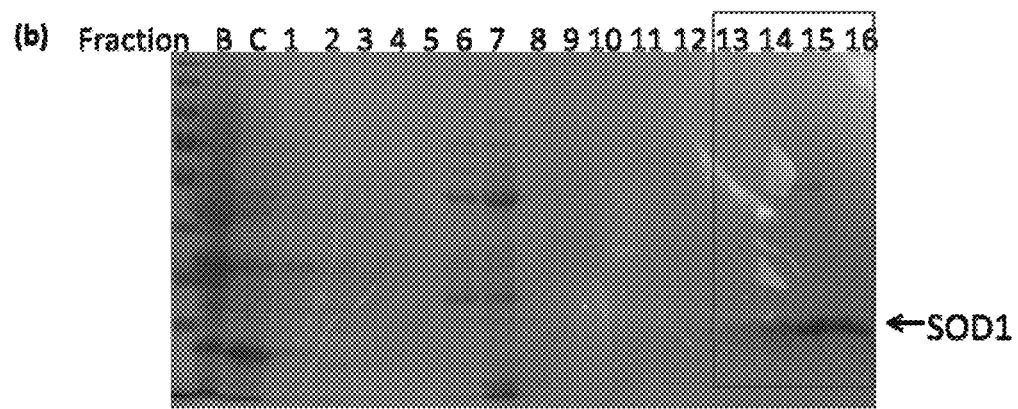
Figure 11:
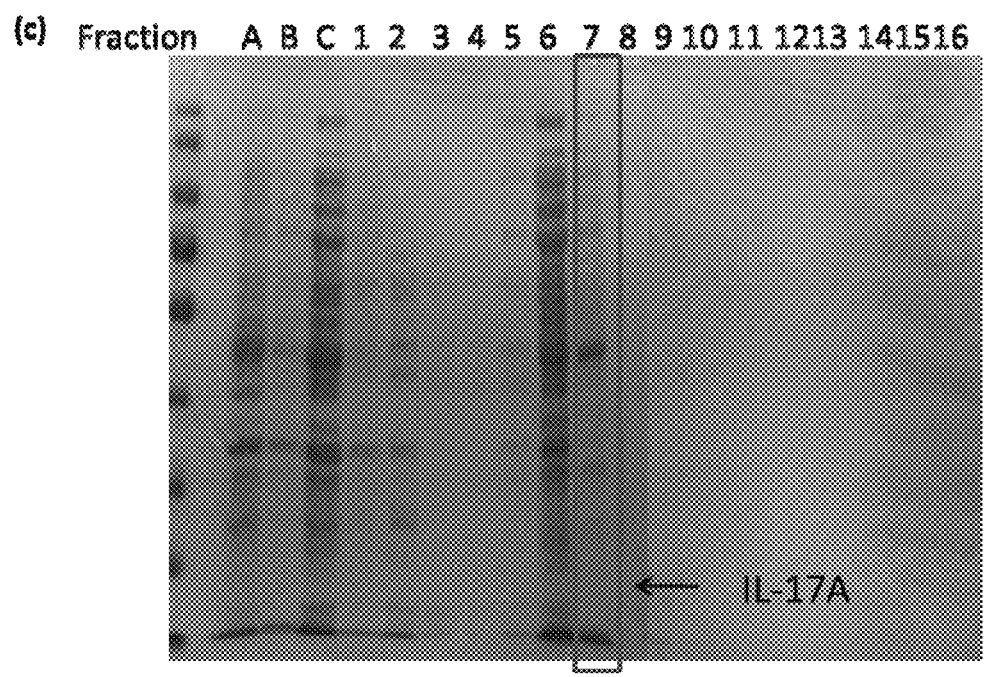

To prove the significance of the biomarkers in the present invention, the cDNA clones are confirmed by restriction enzyme cut (FIG. 8). The transformed bacteria is induced by IPTG to express the biomarker proteins. The protein expression verified by SDS-PAGE and Coomassie Blue staining reveals the protein bands (FIG. 9 a-e). The His-tagged Bmi1, SOD1 and IL-17A proteins are purified by AKTA (FIG. 10 a-c) and then verified by SDS-PAGE and Coomassie Blue staining (FIG. 11 a-c).

Figure 12:
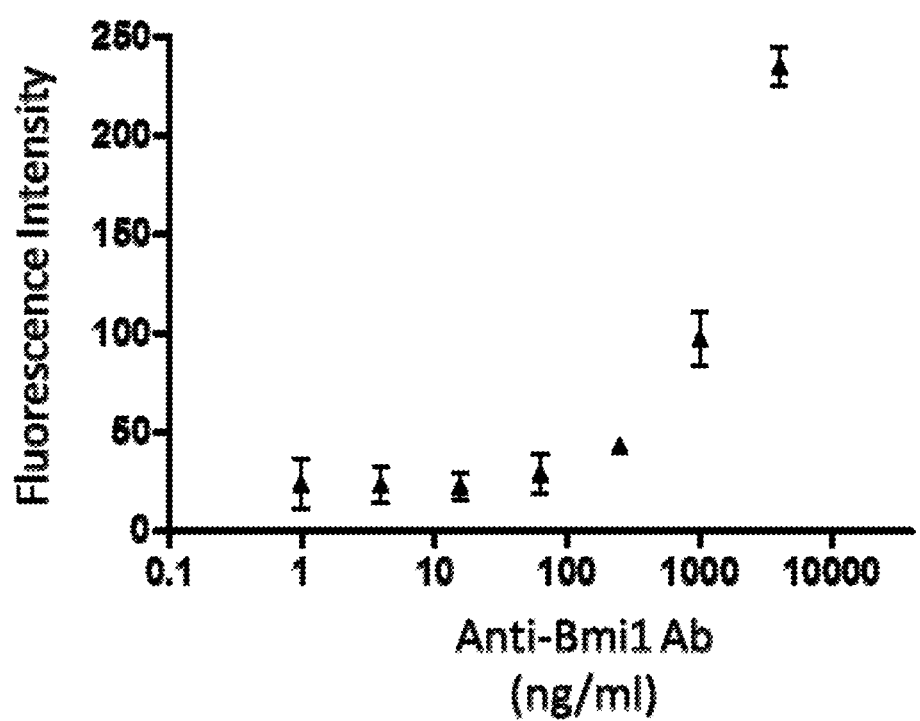
FIG. 12 shows the standard curve showing the fluorescence intensity against the concentration of anti-Bmi1 antibody.

Sensitivity of the test is measured by spiking in a serial dilution of the antibodies. The lowest concentration of the antibody added that can give signal suggests the sensitivity of that particular biomarker. Meanwhile a standard curve is constructed showing the fluorescence intensity of the PE against the serial dilutions of the antibodies (FIG. 12). The standard curve will be used for estimating the concentration of the biomarker specific auto-antibodies in the patient sera by comparing the PE intensity.

Figure 13:
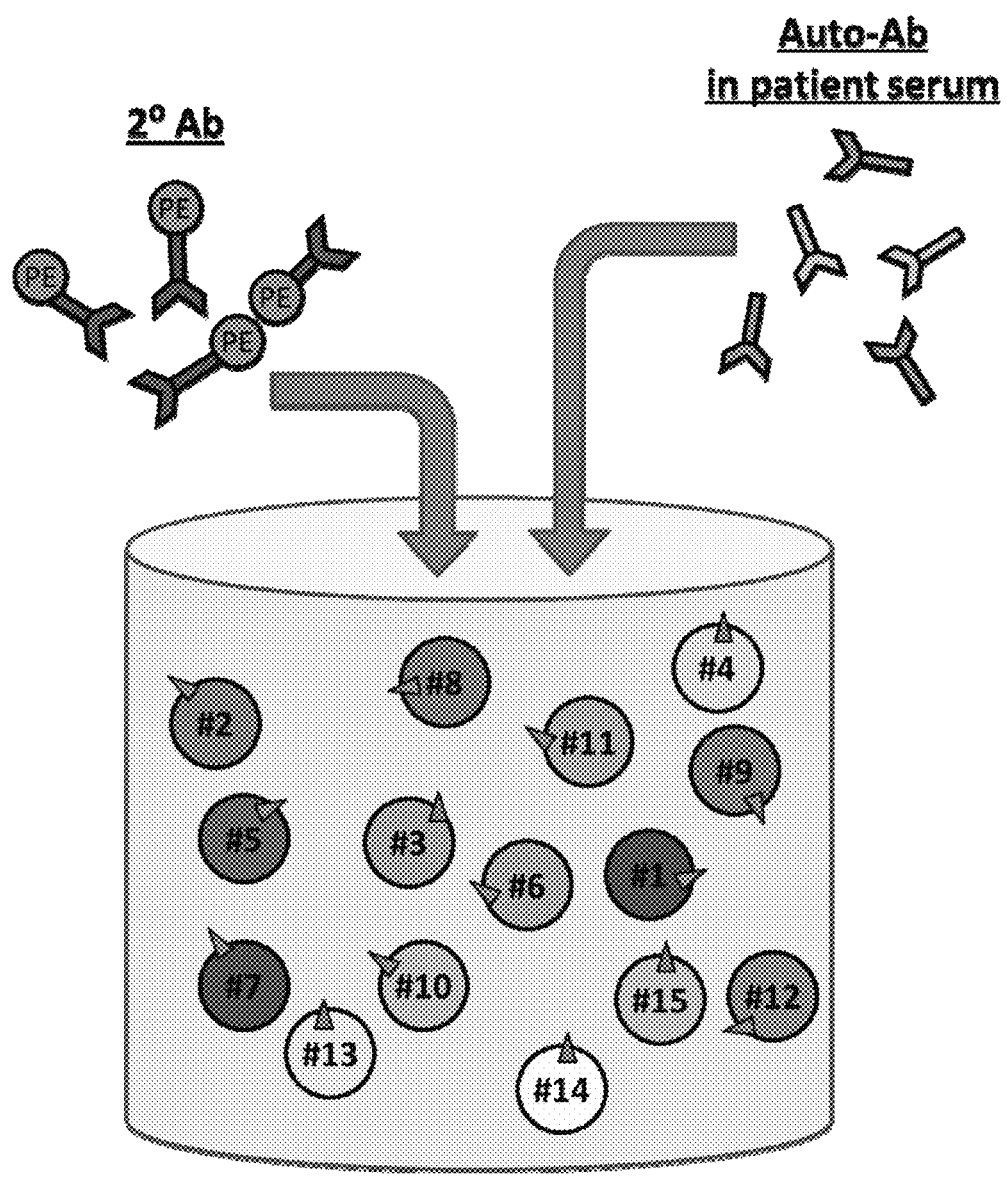
FIG. 13 is a schematic diagram showing the design of the test: Patient serum containing auto-antibodies are mixed to a well containing 15 types of beads corresponding to the 15 biomarkers of the biomarker set, followed by the addition of PE-conjugated secondary antibody.

In the present invention, a multiplex of 15 different Bioplex beads individually giving unique fluorescence are conjugated with the biomarker set and preloaded in the wells of a plate (FIG. 13). To a well, patient serum containing auto-antibodies is loaded and allowed to interact with the biomarker conjugates. The PE-conjugated secondary antibodies are then added and bind to the auto-antibodies. In the machine, the excess secondary antibodies are washed away, the complex comprising the biomarker-bead conjugate and cascade of antibodies are measured individually. The unique fluorescence signal of the Bioplex bead identifies the biomarkers, while the PE signal from the same complex indicates the presence of the auto-antibodies as the primary antibody (FIG. 7). Taken together, the measurement will suggest the presence of auto-antibodies and the relative concentration in the presents' sera.

In a standard randomized trial design, the mean of the relative level of auto-antibodies between the healthy group and patients diagnosed with liver cancer is compared. Student T test is used to analyze the variation significance. The significant difference indicates that the biomarker is specific for liver cancer. After the verification trials, ranges of the concentration of biomarker specific auto-antibodies will be obtained for the liver cancer positive and negative patients and serve as reference point for the future diagnosis. Meanwhile, expression pattern of the auto-antibodies is also compared between liver cancer patients of different stages. The signature patterns of the biomarker expressions will indicate the HCC staging.

Taken together, the measurement of the relative auto-antibodies level and the expression pattern of the biomarkers, the present invention represents a different avenue to complement conventional liver cancer diagnosis. The present invention further enables non-invasive detection of auto-antibodies against the validated targets in patients' sera of the present invention, identifying the extent and the characteristics of the disease. Apart from early detection for stage I liver cancers, the present invention also enables the generation of signature patterns for staging, and the detection of recurrences during a monitoring period of post-mastectomy or post-chemotherapeutic treatment.

EXAMPLES

The following examples are provided by way of describing specific embodiments of this invention without intending to limit the scope of this invention in any way.

Example 1a

Protein Extraction from Patients' Biopsies 500 mg of the paired patients' biopsies (tumor biopsy versus juxtaposed normal tissue) are collected and washed with PBS. The tissues are frozen by submerging into liquid nitrogen and immediately homogenized with pestle and mortar. To the homogenized samples, lysis solution (8M Urea, 4% CHAPS, 2% IPG Buffer, 0.2 mg/ml PMSF) is added, then vortex for at least 5 min until the tissues are completely dispersed. The lysates are then clarified by centrifugation at 14,000 rpm for 10 minutes at 4° C. The supernatants are further cleaned up by 2D Clean Up kit (Amersham) to remove the salt and impurities. The pellets are resuspended with minimum volume of Rehydration Solution (No DTT & IPG Buffer added). The protein concentrations are then measured by Bio-Rad protein assay and aliquots of 200 g/per tube are stored at −70° C.

Example 1b

Resolving Proteins by Two-Dimensional Electrophoresis

To 1 ml rehydration stock solution, 2.8 mg DTT, 5 µl pharmalyte or IPG Buffer, and 2 µl bromophenol blue are added. 50-100 µg of protein sample is added to the 13 cm Immobiline DryStrip (IPG strip) containing 250 µl of rehydration solution. After removing the protective cover, the IPG strip is positioned in the strip holder with the gel side facing down, and overlaid with Cover Fluid to prevent dehydration during electrophoresis. The strip is then placed on to Ettan IPGphor (Amersham) for isoelectric focusing (first dimensional electrophoresis).

After the first-dimensional electrophoresis, the IPG strip is equilibrated with equilibrate solution (6 M Urea 2% SDS, 50 mM Tris HCl pH 6.8, 30% Glycerol, 0.002% Bromophenol blue, 100 mg DTT per 10 ml buffer and 250 mg IAA per 10 ml buffer), and then washed with 1×SDS running Buffer for 4-5 times. The IPG strip is placed on top of the second-dimension gel and overlaid with sealing solution (0.5% Low Melting agarose, 0.002% Bromophenol Blue in 1×SDS running Buffer). The second-dimensional electrophoresis is then carried out at 30 mA for first 15 mM followed by 60 mA for 3-4 h.

Upon the completion of the second dimensional electrophoresis, the gel is removed from the cassette, fixed and stained with silver nitrate. 15 spots representing 15 up-regulated proteins are identified (FIG. 1). To identify the proteins (FIG. 2), the silver stained gel slices are destained and trypsinized to release the protein from the gel for MALDI-TOF analysis.

Example 2a (SEQ ID NO.1)

Amino Acid Sequence of Bmi1

```
MHRTTRIKITELNPHLMCVLCGGYFIDATTIIECLHSFCKTCIVRYLETS
KYCPICDVQVHKTRPLLNIRSDKTLQDIVYKLVPGLEKNEMKRRRDFYAA
HPSADAANGSNEDRGEVADEDKRIITDDEIISLSIEFFDQNRLDRKVNKD
KEKSKEEVNDKRYLRCPAAMTVMHLRKFLRSKMDIPNTFQIDVMYEEEPL
KDYYTLMDIAYIYTWRRNGPLPLKYRVRPTCKRMKISHQRDGLTNAGELE
SDSGSDKANSPAGGIPSTSSCLPSPSTPVQSPHPQFPHISSTMNGTSNSP
SGNHQSSFANRPRKSSVNGSSATSSG
```

Example 2b (SEQ ID NO.2)

Amino Acid Sequence of VCC1

```
MKVLISSLLLLLPLMLMSMVSSSLNPGVARGHRDRGQASRRWLQEGGQEC
ECKDWFLRAPRRKFMTVSGLPKKQCPCDHFKGNVKKTRHQRHHRKPNKHS
RACQQFLKQCQLRSFALPL
```

Example 2c (SEQ ID NO.3)

Amino Acid Sequence of SUMO-4

```
MANEKPTEEVKTENNNHINLKVAGQDGSVVQFKIKRQTPLSKLMKAYCEP
RGLSVKQIRFREGGQPISGTDKPAQLEMEDEDTIDVFQQPTGGVY
```

Example 2d (SEQ ID NO.4)

Amino Acid Sequence of RhoA

MAAIRKKLVIVGDGACGKTCLLIVFSKDQFPEVYVPTVFENYVADIEVDG
KQVELALWDTAGQEDYDRLRPLSYPDTDVILMCFSIDSPDSLENIPEKWT
PEVKHFCPNVPIILVGNKKDLRNDEHTRRELAKMKQEPVKPEEGRDMANR
IGAFGYMECSAKTKDGVREVFEMATRAALQARRGKKKSGCLVL

Example 2e (SEQ ID NO.5)

Amino Acid Sequence of TXN

MVKQIESKTAFQEALDAAGDKLVVVDFSATWCGPCKMIKPFFHSLSEKYS
NVIFLEVDVDDCQDVASECEVKCMPTFQFFKKGQKVGEFSGANKEKLEAT
INELV

Example 2f (SEQ ID NO.6)

Amino Acid Sequence of ET-1

MDYLLMIFSLLFVACQGAPETAVLGAELSAVGENGGEKPTPSPPWRLRRS
KRCSCSSLMDKECVYFCHLDIIWVNTPEHVVPYGLGSPRSKRALENLLPT
KATDRENRCQCASQKDKKCWNFCQAGKELRAEDIMEKDWNNHKKGKDCSK
LGKKCIYQQLVRGRKIRRSSEEHLRQTRSETMRNSVKSSFHDPKLKGNPS
RERYVTHNRAHW

Example 2g (SEQ ID NO.7)

Amino Acid Sequence of UBE2C

MASQNRDPAATSVAAARKGAEPSGGAARGPVGKRLQQELMTLMMSGDKGI
SAFPESDNLEKWVGTIHGAAGTVYEDLRYKLSLEEPSGYPYNAPTVKFLT
PCYHPNVDTQGNICLDILKEKWSALYDVRTILLSIQSLLGEPNIDSPLNT
HAAELWKNPTAFKKYLQETYSKQVTSQEP

Example 2h (SEQ ID NO.8)

Amino Acid Sequence of HDGF2

MARPRPREYKAGDLVFAKMKGYPHWPARIDELPEGAVKPPANKYPIFFFG
THETAFLGPKDLFPYKEYKDKFGKSNRKGFNEGLWEIENNPGVKFTGYQ
AIQQQSSSETEGEGGNTADASSEEEGDRVEEDGKGKRKNEKAGSKRKKSY
TSKKSSKQSRKSPGDEDDKDCKEEENKSSSEGGDAGNDTRNTTSDLQKTS
EGT

Example 2i (SEQ ID NO.9)

Amino Acid Sequence of FGF21

MDSDETGFEHSGLWVSVLAGLLLGACQAHPIPDSSPLLQFGGQVRQRYLY
TDDAQQTEAHLEIREDGTVGGAADQSPESLLQLKALKPGVIQILGVKTSR
FLCQRPDGALYGSLHFDPEACSFRELLLEDGYNVYQSEAHGLPLHLPGNK
SPHRDPAPRGPARFLPLPGLPPALPEPPGILAPQPPDVGSSDPLSMVGPS
QGRSPSYAS

Example 2j (SEQ ID NO.10)

Amino Acid Sequence of LECT2

MFSTKALLLAGLISTALAGPWANICAGKSSNEIRTCDRHGCGQYSAQRSQ
RPHQGVDVLCSAGSTVYAPFTGMIVGQEKPYQNKNAINNGVRISGRGFCV
KMFYIKPIKYKGPIKKGEKLGTLLPLQKVYPGIQSHVHIENCDSSDPTAY
L

Example 2k (SEQ ID NO.11)

Amino Acid Sequence of SOD1

MATKAVCVLKGDGPVQGIINFEQKESNGPVKVWGSIKGLTEGLHGFHVHE
FGDNTAGCTSAGPHENPLSRKHGGPKDEERHVGDLGNVTADKDGVADVSI
EDVISLSGDHCIIGRTLVVHEKADDLGKGGNEESTKTGNAGSRLACGVIG
IAQ

Example 2l (SEQ ID NO.12)

Amino Acid Sequence of STMN4

MTLAAYKEKMKELPLVSLFCSCFLADPLNKSSYKYEADTVDLNWCVISDM
EVIELNKCTSGQSFEVILKPPSEDGVPEFNASLPRRRDPSLEEIQKKLEA
AEEERRKYQEAELLKHLAEKREHEREVIQKAIEENNNFIKMAKEKLAQKME
SNKENREAHLAAMLERLQEKDKHAEEVRKNKELKEEASR

Example 2m (SEQ ID NO.13)

Amino Acid Sequence of Midkine

MQHRGFLLLTLLALLALTSAVAKKKDKVKKGGPGSECAEWAWGPCTPSSK
DCGVGFREGTCGAQTQRIRCRVPCNWKKEFGADCKYKFENWGACDGGTGT
KVRQGTLKKARYNAQCQETIRVTKPCTPKTKAKAKAKKGKGKD

Example 2n (SEQ ID NO.14)

Amino Acid Sequence of IL-17A

MTPGKTSLVSLLLLLSLEAIVKAGITIPRNPGCPNSEDKNFPRTVMVNLN

IHNRNTNTNPKRSSDYYNRSTSPWNLHRNEDPERYPSVIWEAKCRHLGCI

NADGNVDYHMNSVPIQQEILVLRREPPHCPNSFRLEKILVSVGCTCVTPI

VHHVA

Example 2o (SEQ ID NO.15)

Amino Acid Sequence of IL-26

MLVNFILRCGLLLVTLSLAIAKHKQSSFTKSCYPRGTLSQAVDALYIKAA

WLKATIPEDRIKNIRLLKKKTKKQFMKNCQFQEQLLSFFMEDVFGQLQLQ

GCKKIRFVEDFHSLRQKLSHCISCASSAREMKSITRMKRIFYRIGNKGIY

KAISELDILLSWIKKLLESSQ

Example 3a

Expression of Biomarker Set

His tagged plasmids containing cDNA inserts encoding the biomarker set is transformed into DH5 competent cells (301, FIG. 3). Single colony is picked and allowed to grow in bacterial culture (302). The number of plasmid is expanded and extracted from the bacteria by miniprep. The plasmid is further transformed into BL21DE3 or BL21DE3pLysS competent cells. Transformed bacteria are selected and grew in 2×100 ml LB medium. When the bacterial culture reaches the optical density of 0.06, 200 µM of IPTG is added to 100 ml bacterial culture (303). Another 100 ml of bacterial culture without IPTG is used as negative control. The bacterial cultures are incubated at 30° C. with shaking. 500 µl of the bacterial cultures are saved and stored at −20° C. 3 h after the incubation and in the next morning after incubating overnight.

Bacterial cultures with and without IPTG induction are mixed together in a 500 ml centrifuge bottle. Bacterial cells are collected by centrifugation at 9000 rpm for 20 min at 4° C. (304). 500 µl of supernatant is saved as another negative control and the remaining supernatant is discarded. The bacterial cultures and negative controls collected in different points are run on a SDS-PAGE to resolve the protein (305). The gel is then stained with Coomassie Blue overnight. After destaining the gel, the protein induction can be confirmed by checking the size and comparing with the negative controls.

Example 3b

Protein Purification for Biomarker Set

The bacterial cell pellets are resuspended in 10 ml solubilization buffer by vortex at room temperature. Keeping the resuspended cells in 50 ml centrifuge tube on ice, the cells are completely lysed by sonication at amplitude 70% 10 rounds of 30 s with interval of 30 s (401, FIG. 4). The lysed cells are centrifuged at 10,000 rpm for 1 h at 4° C. (402). Supernatants are transferred into dialysis tubing and submerged in 1 L unfiltered starting buffer for 4-6 h at 4° C. with constant stirring (403). Dialysis is continued with another 1 L starting buffer overnight. The supernatant is further filtered with 0.22 µm filter disc and syringe. To the AKTA machine equipped with 0.1M Nickel sulfate charged HiTrap chelating column (404), filtered samples are loaded (405). A program is set at the AKTA machine that the eluent is collected in fractions automatically (406). Proteins purified from different fractions are checked by SDS-PAGE analysis (407).

Example 4a

Protein Coupling with Bio-Plex Beads

The purified proteins of the biomarker set are coupled with Bio-Plex beads (Bio-Rad) (501) according to the manufacturer's manual. In brief, uncoupled bead is vortexed for 30 s and then sonicated for 15 s. 1,250,000 beads are collected in a reaction tube by centrifugation of 100 µl bead at maximum speed for 4 min. After washing with 100 µl bead wash buffer by centrifugation, the beads are resuspended in 80 µl bead activation buffer. To the beads 10 µl 50 mg/ml freshly prepared S-NHS and 10 µl 50 mg/ml freshly prepared EDAC are added, followed by 20 min incubation in dark at room temperature (FIG. 6). The beads are then washed with 150 µl PBS twice.

To the washed beads, 10 µg proteins are added and the total volume is topped up with PBS to 500 µl, and allowed to incubate for 2 h with shaking in dark. Supernatant is removed after centrifugation at maximum speed for 4 min 250 µl blocking buffer is added to the beads and shook in dark for 30 min, followed by centrifugation at maximum speed for 4 min and removal of supernatant. The beads are briefly washed and then resuspended in the storage buffer for storage at 4° C. The numbers of the beads are counted with a hemocytometer.

Example 4b

Validation of Protein-Bead Coupling

To a HTS 96 well plate, 50 µl of conjugated Bio-Plex beads (100 beads/µl) is added to react with primary followed by secondary antibodies (502). A serial dilution of the commercially available primary anti-bodies against the biomarker set is prepared as 8,000, 4,000, 1,000, 250, 62.5, 15.625, 3.906, 0.977, 0.244 and 0.061 ng/ml. 50 µl of each dilution is added to each well. Two negative controls are performed by excluding the primary antibodies, and both primary and secondary antibodies in the wells. The plate is then sealed with a foil and kept on a shaker for 30 min at 350 rpm, avoiding exposure to light.

After incubation, the beads are washed three times with 150 µl PBS. 50 µl of PE-conjugated secondary antibody (8,000 ng/ml) is added into each well except negative controls. The plate is sealed again and incubated in dark for 30 min with shaking. Excess antibodies are then washed away by PBS. The Bio-Plex machine is calibrated with the calibration kit and validation kit. After the HTS plate is loaded to the machine, signals from both the Bio-Plex beads and the PE conjugated at the secondary antibodies (503) are measured (schematic diagram is shown in FIG. 7). A calibration curve is generated by Logistic-SPL.

Example 4c

Collection of Serum Samples and Measurement of Auto-Antibodies by BioPlex System Whole-blood samples are clotted by standing at 37° C. for 1 h. Sera containing the auto-antibodies is collected at the supernatant after centrifugation at 1000 g room temperature for 10 min. The serum samples are diluted with PBS when necessary. To a HTS plate preloaded with Bioplex beads conjugated with biomarker set, the serum samples are loaded and incubated for 30 min with shaking (FIG. 13). Similar to the steps described in Example 4b, to the PBS washed beads, 50 μl of PE-conjugated secondary antibody (8000 ng/ml) is added, followed by shaking for another 30 min. After three rounds of washing, the plate is loaded to the Bio-Plex machine and the fluorescence signal is measured (504). The concentration of the auto-antibodies can then be calculated from the standard curves.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments are chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

INDUSTRIAL APPLICABILITY

The presently claimed method and kit comprising the 15 identified biomarkers can not only be used to identify and quantify the presence of auto-antibodies in the patents' sera in order to detect and/or stage the liver cancer, but are also useful in drug development targeting these markers for specifically treating the liver cancer.

---

What is claimed is:

1. A kit for detecting HCC biomarker auto-antibodies to a plurality of hepatocellular carcinoma (HCC) biomarkers in a patient's serum, the kit comprising:
   a. a set of 15 hepatocellular carcinoma (HCC) biomarker conjugates comprising HCC biomarker proteins set forth in SEQ ID NOs: 1-15, wherein each protein set forth in SEQ ID Nos: 1-15 is coupled to a different fluorescent microsphere bead having a different emission wavelength; and
   b. a PE-conjugated secondary antibody capable of binding to all of the HCC biomarker auto-antibodies to the plurality of HCC biomarkers wherein the HCC biomarkers are Bmi-1, VCC1, SUMO-4, RhoA, TXN, ET-1, UBE2C, HDGF2, FGF21, LECT2, SOD1, STMN4, Midkine, IL-17A and IL26 as set forth in SEQ ID NOs: 1-15.

2. The kit of claim 1, wherein the kit is capable of detecting an auto-antibody to any one of the hepatocellular carcinoma (HCC) biomarker present in the patient's serum when the auto-antibody is present at an amount as low as about 0.15 ng/mL.

* * * * *